United States Patent
Takagi et al.

(10) Patent No.: US 6,569,333 B1
(45) Date of Patent: May 27, 2003

(54) RESTORING SOIL AND PREVENTING CONTAMINATION OF GROUND WATER

(75) Inventors: Kazuhiro Takagi, 11-916-101, Namiki 4-chome, Tsukuba-shi, Ibaraki 305-0044 (JP); Yuuichi Yoshioka, Kochi (JP)

(73) Assignees: National Institute for Agro-Environmental Sciences Independent Administrative Institute, Tsukuba (JP); Toyo Denka Kogyo Co., Ltd., Kochi (JP); Kazuhiro Takagi, Tsukuba (JP)

( * ) Notice: Subject to any disclaimer, the term of this patent is extended or adjusted under 35 U.S.C. 154(b) by 0 days.

(21) Appl. No.: 09/744,996
(22) PCT Filed: Jun. 22, 1999
(86) PCT No.: PCT/JP99/03324
§ 371 (c)(1), (2), (4) Date: Apr. 20, 2001
(87) PCT Pub. No.: WO00/78923
PCT Pub. Date: Dec. 28, 2000

(51) Int. Cl.[7] .............................. C02F 3/00; C12M 1/00; C12N 11/16; B09B 3/00
(52) U.S. Cl. ........................ 210/610; 210/747; 435/174; 435/262.5; 435/289.1
(58) Field of Search .................. 210/610, 611, 210/615, 616, 617, 747, 150, 151, 170, 915; 435/174, 262.5, 289.1

(56) References Cited

U.S. PATENT DOCUMENTS

| | | | | |
|---|---|---|---|---|
| 4,608,163 A | * | 8/1986 | Yohe et al. ................. | 210/150 |
| 4,849,360 A | * | 7/1989 | Norris et al. ................ | 435/264 |
| 5,217,616 A | * | 6/1993 | Sanyal et al. ............... | 210/150 |
| 5,266,482 A | * | 11/1993 | Kiener et al. ............. | 435/252.2 |
| 5,270,203 A | * | 12/1993 | Kiener ..................... | 435/252.1 |
| 5,284,767 A | * | 2/1994 | Kiener et al. ............ | 435/252.1 |
| 5,879,555 A | * | 3/1999 | Khudenko .................. | 210/615 |

* cited by examiner

Primary Examiner—Chester T. Barry
(74) Attorney, Agent, or Firm—Rader, Fishman & Grauer, PLLC

(57) ABSTRACT

The object of the present invention is to restore soil and prevent contamination of ground water by decomposing an organic compound with decomposing microorganisms in soil contaminated with an agricultural chemical or other organic compound.

The present invention discloses an accumulation method for isolated decomposing microorganisms comprising: accumulating decomposing microorganisms of a species able to decompose a specific organic compound in a porous material that is able to adsorb said organic compound while also having a countless number of pores that facilitate habitation by said decomposing microorganisms; wherein, by inoculating only said decomposing microorganisms into a porous material, forming an accumulation layer composed of that inoculated porous material, and perfusing that accumulation layer with an inorganic salt medium having only said organic compound for its carbon source and nitrogen source, said decomposing microorganisms are accumulated in the porous material in a state of high density, and a decomposing microorganism retentive carrier obtained in this manner is buried directly in contaminated soil.

6 Claims, 8 Drawing Sheets

FIG.2

| Microhabitat | pH (H₂O) | BET single-point method specific surface area (m²/g) | Ratio of cumulative pore volume to pore diameter (%) | | | | | | | | |
|---|---|---|---|---|---|---|---|---|---|---|---|
| | | | Pore diameter (μm) | | | | | | | | |
| | | | 200~100 | 100~50 | 50~20 | 20~10 | 10~5 | 5~1 | 1~0.003 | | |
| A | 7.8 | 99.9 | 3.0 | 6.5 | 9.8 | 6.4 | 5.8 | 16.5 | 52.3 | | |
| B | 5.5 | 72.1 | 5.4 | 4.3 | 9.0 | 6.6 | 5.4 | 9.3 | 60.1 | | |
| C | 8.1 | 555.7 | 0.0 | 2.5 | 20.0 | 25.4 | 7.5 | 22.5 | 22.1 | | |

FIG.5

| Sampling site | Sampling depth (cm) | Moisture content (%) | pH (H₂O) | pH (KCl) | T-C (%) | T-N (%) | C/N |
|---|---|---|---|---|---|---|---|
| Golf course | 5~10 | 26.6 | 7.2 | 6.8 | 1.91 | 0.18 | 10.3 |

FIG.14

| | Initial quintozene concentration in contaminated soil for decomposition<br>10 mg/kg d.s. | | Total residual amount<br>mg/kg | Decomposition removal rate<br>% |
|---|---|---|---|---|
| Case of using decomposing microorganism accumulated retentive carrier shown in Fig.12 | Residual quintozene concentration in contaminated soil for decomposition after decomposition testing<br>0.035 mg/kg d.s. | Residual quintozene concentration in decomposing microorganism accumulated retentive carrier after decomposition testing<br>0.004 mg/kg d.m. | 0.04 | 99.61 |
| Case of using unaccumulated microhabitat A shown in Fig.13 | Residual quintozene concentration in contaminated soil for decomposition after decomposition testing<br>8.70 mg/kg d.s. | Residual quintozene concentration in unaccumulated artificial microhabitat A after decomposition testing<br>0.32 mg/kg d.s. | 9.02 | 9.84 |

FIG.15

| | Quintozene-decomposing microorganism count in perfusion liquid | | |
|---|---|---|---|
| | Measurement period | | |
| | Week 1 | Week 2 | Week 3 |
| Case of decomposition testing shown in Fig.12 | 0 | 0 | 0 |
| Case of decomposition testing shown in Fig.13 | 0 | 0 | 0 |

RESTORING SOIL AND PREVENTING CONTAMINATION OF GROUND WATER

TECHNICAL FIELD

The present invention relates to technology for restoring soil and preventing contamination of ground water by decomposing organic compounds by decomposing microorganisms in, for example, soil that has been contaminated by organic compounds such as agricultural chemicals. In particular, the present invention relates to technology for rapidly and efficiently accumulating and isolating only those decomposing microorganisms of a species that is capable of decomposing poorly degradable organic contaminants contained in soil, and to technology for restoring contaminated soil and preventing contamination of ground water by applying a retentive carrier for decomposing microorganisms that has accumulated those isolated decomposing microorganisms directly to contaminated soil.

BACKGOROUND ART

The restoration of soil contaminated by organic compounds such as agricultural chemicals by decomposing microorganisms along with the prevention of ground water contamination caused by those organic compounds has conventionally been considered to be a useful technology. For example, if decomposing microorganisms that decompose or detoxify organic compounds such as agricultural chemicals are present among microorganisms that thrive in soil, and the capabilities of these decomposing microorganisms is utilized, contaminants such as agricultural chemicals can be removed from soil.

However, in the natural state, due to the low density of decomposing microorganisms having the ability to decompose specific organic compounds, it has not been possible to effectively prevent the retention or diffusion of contaminants in the environment.

Consequently, if it were possible to accumulate only decomposing microorganisms able to decompose specific organic compounds at a higher density and in a state in which they possess decomposing activity, it would be possible to effectively realize restoration of contaminated soil and prevention of ground water contamination.

However, in the case of methods for culturing decomposing microorganisms carried out in the prior art, such as a method in which only a specific decomposing microorganism is inoculated into and grown in a liquid medium or solid medium that only uses a specific organic compound for its carbon source and nitrogen source, although only a specific decomposing microorganism can be cultured at high density, even if only that cultured decomposing microorganism is applied directly to an environment such as contaminated soil, that cultured decomposing microorganism hardly ever demonstrates its decomposing activity in a stable manner for a long period of time.

This is because, in the case of directly applying only a specific decomposing microorganism to contaminated soil, as a result of being subjected to the physiochemical properties of the contaminated soil, being preyed on by the large numbers of Protozoa and other organisms that thrive in the contaminated soil, or being unable to acquire a niche due to competition with other microorganisms, that specific decomposing microorganism is destroyed. In addition, this is also because, if the target organic compound to serve as the nutrient source (carbon source and nitrogen source) of a specific decomposing microorganism is adsorbed into a soil solid phase and is in a state that cannot be supplied to the specific decomposing microorganism, namely if it is in a state of low bioavailability, the decomposing activity of that specific decomposing microorganism cannot be demonstrated and maintained.

DISCLOSURE OF THE INVENTION

In consideration of these circumstances, the object of the present invention is to provide a technology for rapidly and efficiently accumulating a decomposing microorganism of a species that is capable of decomposing a specific organic compound in a state in which that decomposing activity is demonstrated in a stable manner for a long period of time, and for restoring contaminated soil and preventing contamination of ground water by using a decomposing microorganism retentive carrier that has accumulated that decomposing microorganism to decompose organic compounds present in contaminated soil.

The present invention is based on new findings obtained from research on an improved soil perfusion method previously proposed by the inventors of the present invention (Japanese Patent Application No. Hei 9-30176). The improved soil perfusion method proposed by the inventors of the present invention refers to using a porous material, which together with having a function that adsorbs a specific organic compound, also has a countless number of pores in a state that facilitates habitation by decomposing microorganisms having the ability to decompose that organic compound, to form an accumulation soil layer composed of this porous material and soil in which said decomposing microorganisms thrive, followed by continuously perfusing an inorganic salt medium having only the target organic compound for its carbon source and nitrogen source through this accumulation soil layer, thereby rapidly accumulating decomposing microorganisms in said porous material.

As a result, the inventors of the present invention considerably improved the accumulation and isolation rates of decomposing microorganisms to an extent that was unable to be realized with the soil perfusion method of the prior art. In other words, in this improved soil perfusion method, the porous material efficiently adsorbs carbon and nitrogen sources contained in the inorganic salt medium, namely the organic compound that is contaminating the soil, and due to the favorable conditions imparted by its pores, decomposing microorganisms grow and function actively by using the adsorbed organic compound as a nutrient source (carbon source and nitrogen source). As a result of effectively combining these factors, organic compounds that have been efficiently adsorbed into the pores are efficiently assimilated and decomposed by decomposing microorganisms within the pores, thereby realizing their rapid accumulation.

Decomposing microorganisms that accumulate in the porous material according to this improved soil perfusion method are in a state in which decomposing microorganisms of a species that has the ability to decompose a specific organic compound are selectively accumulated. However, the decomposing microorganisms that have accumulated in the porous material are actually in the state of a mixture with several species of bacteria not directly involved in decomposition.

Therefore, the inventors of the present invention attempted to apply the above improved soil perfusion method in order to accumulate only decomposing microorganisms of a species that is capable of decomposing a specific organic compound in a purified state. More specifically, according to the above improved perfusion method, a porous material that had accumulated a specific decomposing microorganism was first used as the inoculation source to inoculate a fresh porous material (in which decomposing microorganisms had not yet been accumulated) in a state of being mixed with several species of bacteria not directly involved in decomposition. By then perfusing an inorganic salt medium having for its carbon source and nitrogen source only the organic compound that serves as the nutrient source of that specific decomposing microorganism, only the specific decomposing microorganism was purified and accumulated in the fresh porous material.

Although it is possible that the decomposing microorganism accumulated in the porous material following the above purification is a single species of decomposing microorganism, since normally two to three species of decomposing microorganisms are present, in order to accumulate only those decomposing microorganisms that decompose a specific organic compound, the porous material in which decomposing microorganisms are accumulated following purification was crushed, mixed dilutions of the crushed porous material were prepared using phosphate buffer as diluent, those mixed dilutions were plated onto inorganic salt agar media that uses only the specific organic compound for its carbon source and nitrogen source, and microorganisms were picked from those portions of high decomposing activity formed on the inorganic salt agar medium (clear zones) to isolate only specific decomposing microorganisms.

Moreover, only specific decomposing microorganisms picked and isolated from the clear zone formed on inorganic salt agar media were used as an inoculation source to inoculate a fresh porous material, and an inorganic salt medium having only a specific organic compound for its carbon source and nitrogen source was perfused through that porous material. As a result, it was ultimately determined that only decomposing microorganisms of a species that is able to decompose a specific organic compound were able to be accumulated in the porous material at a high density in an extremely purified state. Decomposing microorganisms accumulated at high density and in an extremely purified state in a porous material in this manner were determined to decompose an organic compound adsorbed to the porous material in a stable manner.

According to the research results of the inventors of the present invention as described above, it was determined that the technology described below enables accumulation of decomposing microorganisms. To begin with, as is described in claim 1, only decomposing microorganisms of a species able to decompose a specific organic compound are inoculated into a porous material, which together with being able to adsorb said organic compound, has a countless number of pores that facilitate habitation by said decomposing microorganisms, an accumulation layer is formed from the inoculated porous material, and the inorganic salt medium, having only the above organic compound for its carbon source and nitrogen source, is perfused through this accumulation layer.

As a result, only a decomposing microorganism of a species that is able to decompose a specific organic compound can be accumulated at high density in a porous material both rapidly and efficiently. Decomposing microorganisms accumulated in a porous material in this manner are able to demonstrate and maintain stable decomposing activity on the organic compound adsorbed to the porous material.

In both that previously described and that described below, decomposing microorganisms of a species that are able to decompose a specific organic compound refer to that which employs the concept that includes not only the case of a mixture of a plurality of species of decomposing microorganisms, but also the case of only a single species of decomposing microorganism.

It is necessary to identify only those decomposing microorganisms in order to inoculate only a species of decomposing microorganism able to decompose a specific organic compound into a porous material. In this case, as is described in claim 2, it is preferable to inoculate a group of bacteria containing a species of decomposing microorganisms that is able to decompose a specific organic compound onto an inorganic salt agar medium that only has said organic compound for its carbon source and nitrogen source, pick microorganisms from a portion of high decomposing activity that have formed on the inorganic salt agar medium (clear zone), and inoculate only the isolated decomposing microorganism.

When decomposing microorganisms picked and isolated from a portion of high decomposing activity formed on the inorganic salt agar medium, namely the portion at which decomposing microorganisms able to decompose a specific organic compound are thriving, such as decomposing microorganisms obtained by cutting out a portion of a clear zone in a state in which the decomposing microorganisms are accompanied by inorganic salt agar medium, are inoculated into a porous material, only those decomposing microorganisms of a species that is able to decompose a specific organic compound can be rapidly and efficiently accumulated. This is because, although there is a method in which decomposing microorganisms are grown and inoculated from so-called liquid medium, according to current research results of the inventors of the present invention, an inoculation method consisting of cutting out clear zones formed on inorganic salt agar medium for each agar medium has been confirmed to allow rapid and efficient accumulation in the present invention.

Moreover, in the case of accumulating only a decomposing microorganism of a species that is able to decompose an organic contaminant in which a specific organic compound can be contained in contaminated soil by selecting that decomposing microorganism from contaminated soil, as described in claim 3, it is preferable to accumulate only said decomposing microorganism in a porous material by removing an accumulated porous material that has accumulated decomposing microorganisms obtained according to the above improved soil perfusion method from an accumulation soil layer, perfusing the inorganic salt medium having only said organic contaminant for its carbon source and nitrogen source through the accumulation soil layer, removing the accumulated porous material from the accumulation soil layer, performing washing treatment that removes soil adhering to the removed accumulated porous material, using the washed accumulated porous material as an inoculation source to inoculate an accumulation layer formed only from a fresh porous material, using a group of bacteria accumulated by purifying in the fresh porous material by perfusing an inorganic salt medium having only said organic contaminant for its carbon source and nitrogen source through the accumulation layer, and using the inorganic salt agar medium described in claim 2 to isolate the decomposing microorganisms.

When this is done, only decomposing microorganisms having high decomposing activity for a specific organic contaminant can be selected from bacteria thriving in contaminated soil, making it possible to rapidly and efficiently accumulate those decomposing microorganisms in a porous material at high density. This is effective in the case of decomposing an organic chlorine-based compound such as an agricultural chemical known to be a soil contaminant, and according to research conducted by the inventors of the present invention, has been demonstrated by using soil containing the poorly degradable organic chlorine-based compounds of simazine (CAT) and quintozene (PCNB).

Porous materials in which only decomposing microorganisms of a species able to decompose a specific organic compound are accumulated by the accumulation method for isolated decomposing microorganisms as claimed in the present invention offer the following advantages as decomposing microorganism retentive carriers. These advantages consist of these porous materials allow decomposing microorganisms to be handled extremely easily and being able to be easily applied to soil. In addition, in the case of using charcoal or other ligneous material as a porous material, there are no detrimental effects on the soil when applied directly to the soil, and these materials have properties that allow contaminants in the form of organic compounds to be adsorbed efficiently.

Moreover, as is described in claim 6, by using a porous material that has accumulated only a specific decomposing microorganism obtained by the aggregation method for isolated decomposing microorganisms as claimed in the present invention as a decomposing microorganism retentive carrier, and burying that retentive carrier in contaminated soil containing the target organic compound, the organic compound in the contaminated soil can be decomposed, making it possible to restore contaminated soil and prevent ground water contamination.

In the case of burying the decomposing microorganism retentive carrier as claimed in the present invention in contaminated soil, it is preferable to thoroughly mix with the contaminated soil. This is because, when buried after thoroughly mixing with the contaminated soil in this manner, there is greater contact between the contaminated soil and decomposing microorganism retentive carrier, resulting in the target organic compound being uniformly adsorbed onto the porous material. In addition, it is also preferable to perfuse an inorganic salt medium having only the target organic compound for its carbon source and nitrogen source through the contaminated soil in which the decomposing microorganism retentive carrier is buried. This is because, when this is done, recovery treatment of the contaminated soil can be performed rapidly and efficiently. Since organic compounds contained in contaminated soil flow through the soil due to penetration of sprayed water and rain water, a specific organic compound contained in the contaminated soil can be decomposed simply by burying the decomposing microorganism retentive carrier as claimed in the present invention in the contaminated soil without having to perfuse with the inorganic salt medium as described above.

Decomposing a specific organic compound in contaminated soil by a specific decomposing microorganism accumulated in a porous material even if the decomposing microorganism retentive carrier as claimed in the present invention is buried in contaminated soil in this manner is thought to be possible for the reasons indicated below.

To begin with, since decomposing microorganisms thrive inside pores of a porous material in the decomposing microorganism retentive carrier as claimed in the present invention, the porous material fulfills the role of a so-called shelter, and is presumed to protect the accumulated specific decomposing microorganisms from the physicochemical properties of the contaminated soil, from being preyed on by the large numbers of Protozoa and other organisms that thrive in the contaminated soil, or from competition with other microorganisms over acquiring a niche and so forth. Since the porous material efficiently adsorbs organic compounds in contaminated soil, by providing a nutrient source (carbon source and nitrogen source) of a specific decomposing microorganism in the pores, a state of high bioavailability results, which is presumed to enable decomposing activity to be demonstrated and maintained in a stable manner.

Thus, according to the present invention, restoration treatment of contaminated soil can be performed rapidly and efficiently, and even if an organic compound such as an agricultural chemical is again sprayed on the contaminated soil, since the decomposing microorganism retentive carrier is buried in the contaminated soil, the sprayed, for instance, organic compound is decomposed, thereby preventing its retention and diffusion into the soil. Entry of organic compounds present in the soil into ground water is also avoided, thereby making it possible to prevent contamination of ground water. Various applications can be considered based on these characteristics of the present invention. Examples of these include, with respect to aqueous systems, domestic wastewater lines, agricultural wastewater lines in areas with rice paddies and the wastewater lines of golf courses, with respect to soil systems, top and bottom soil containing environmental contaminants, bottom soil of the greens of golf courses, bottom soil of industrial waste processing sites and bottom soil of organic waste storage sites at factories and so forth, and with respect to combined aqueous and soil systems, soil at coastlines contaminated by runoff oil. Direct application of the decomposing microorganism retentive carrier as claimed in the present invention to these applications results in effective environmental protection.

The phenomenon in the present invention described above is an extremely rare example throughout the world in technical fields utilizing microorganisms. Consequently, the present invention can be said to be an extremely beneficial technology especially today when there is a dire need for preventing environmental contamination expanding on a global scale as quickly as possible for the purpose of restoring the contaminated environment (bioremediation).

BRIEF DESCRIPTION OF THE DRAWINGS

FIG. 2 is a table of physical properties of each artificial microhabitat used in the embodiments.

FIG. 5 is a table showing the physicochemical properties of soil provided for use in decomposition testing.

FIG. 14 is a table showing the results of measuring the amount of residual quintozene following decomposition testing of quintozene.

FIG. 15 is a table showing the results of measuring the amount of outflow of quintozene decomposing microorganisms into perfusion liquid during decomposition testing of quintozene.

DESCRIPTION OF REFERENCE NUMERALS

1 Soil layer tank
1' Accumulation layer tank
2 Accumulation soil layer
2' Accumulation layer
2" Decomposition soil layer
3 Inorganic salt medium
4 Liquid storage tank

BEST MODE FOR CARRYING OUT THE PRESENT INVENTION

The following provides an explanation of the examples of the present invention. To begin with, an explanation is provided of the case of the poorly degradable organic chlorine-based agricultural chemical simazine (CAT) as a first example of the present invention.

FIRST EXAMPLE

Accumulation of decomposing microorganisms that decompose simazine by the improved soil perfusion method proposed by the inventors of the present invention was performed under the conditions shown in Table 1 below.

TABLE 1

Figure 1:
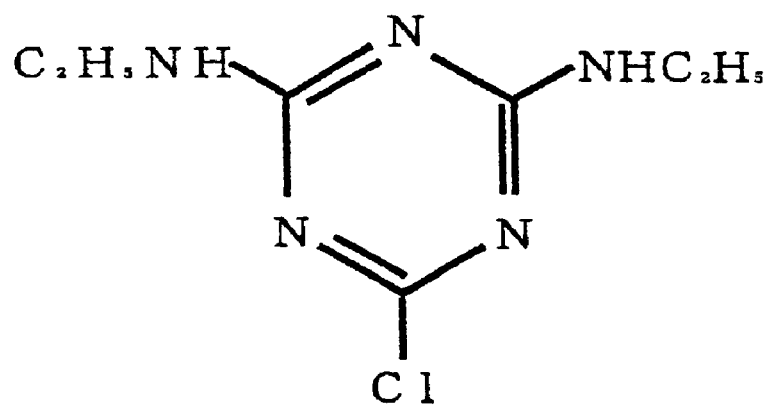
FIG. 1 is the structural formula of simazine.

| Test agricultural chemical | Simazine standard (structural formula shown in FIG. 1) |
|---|---|
| Test soil for accumulation | Field soil containing simazine, passed through a sieve to a size of 2 mm or less |
| Perfusion liquid | Inorganic salt medium containing 5 mg/l of simazine for the carbon source and nitrogen source |
| Perfusion conditions | 25° C., dark location |

In addition, artificial microhabitats A through C having the physical properties respectively shown in FIG. 2 were used for the porous materials used during accumulation (hereinafter, to be referred to as artificial microhabitats). Artificial microhabitats A through C in FIG. 2 indicate the artificial microhabitats shown in Table 2 below.

TABLE 2

| A | 5 to 10 mm pieces of carbonized woody material obtained by ordinary baking of broad-leafed trees (normal burning temperature: 500° C., to apply similarly hereinafter) |
|---|---|
| B | 5 to 10 mm pieces of carbonized woody material obtained by ordinary baking of chitosan-treated broad-leafed trees |
| C | 5 to 10 mm pieces of carbonized woody material obtained from coniferous trees baked for 8 hours at 1000° C. |

Figure 3:
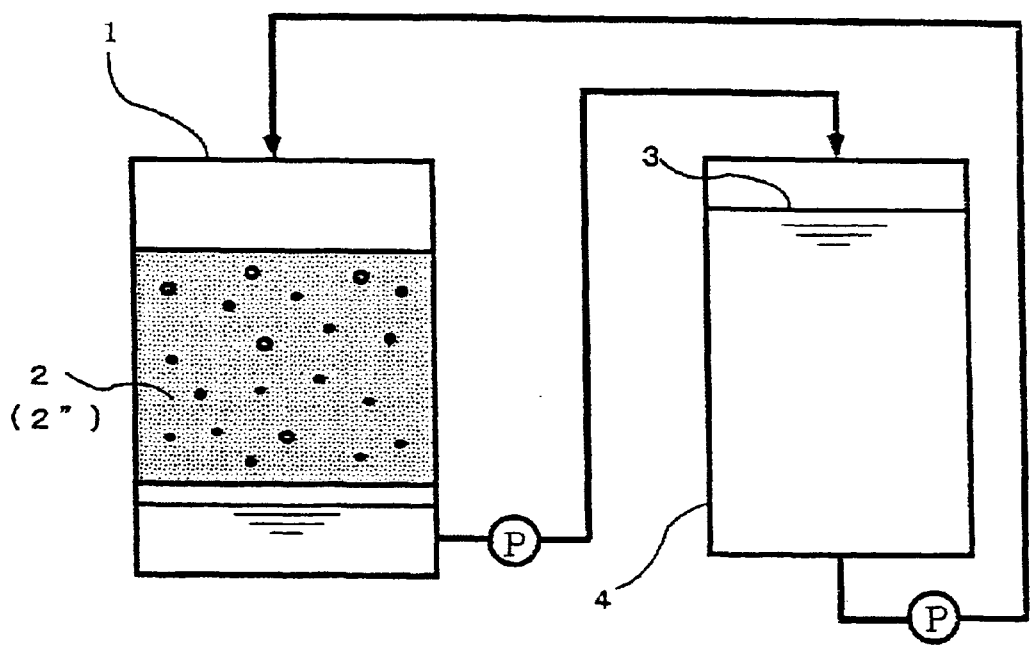
FIG. 3 is a schematic drawing of a perfusion device used in accumulation, isolation and decomposition testing of the embodiments.

The decomposing microorganisms that decompose simazine in the first example were first accumulated from the test soil for accumulation in artificial microhabitat B in the manner described below. As shown in FIG. 3, an accumulation soil layer 2 was formed in a soil layer tank 1 having a capacity of 500 ml. This accumulation soil layer 2 was formed by mixing 2 g of artificial microhabitat B fragmented into pieces measuring 5 to 10 mm into 40 g of test soil for accumulation. An inorganic salt medium 3, having the test agricultural chemical, simazine, for its only carbon source and nitrogen source (simazine concentration: 5 mg/l, liquid volume: 300 ml) was perfused from a liquid storage tank 4 into the accumulation soil layer 2, after which accumulation was performed in a dark location at 25° C. The perfusion liquid in the form of the inorganic salt medium 3 was replaced with fresh medium once a week, and accumulation was performed for about 3 weeks.

After this accumulation treatment, artificial microhabitat B was removed from the accumulation soil layer 2 and was removed of adhered soil by immersion in sterile distilled water and ultrasonic washing treatment. The treatment for isolating and accumulating only those decomposing microorganisms that decompose simazine (hereinafter, to be referred to as simazine-decomposing microorganisms) from the accumulated artificial microhabitat B following this washing treatment was performed in the manner described below.

Figure 4:
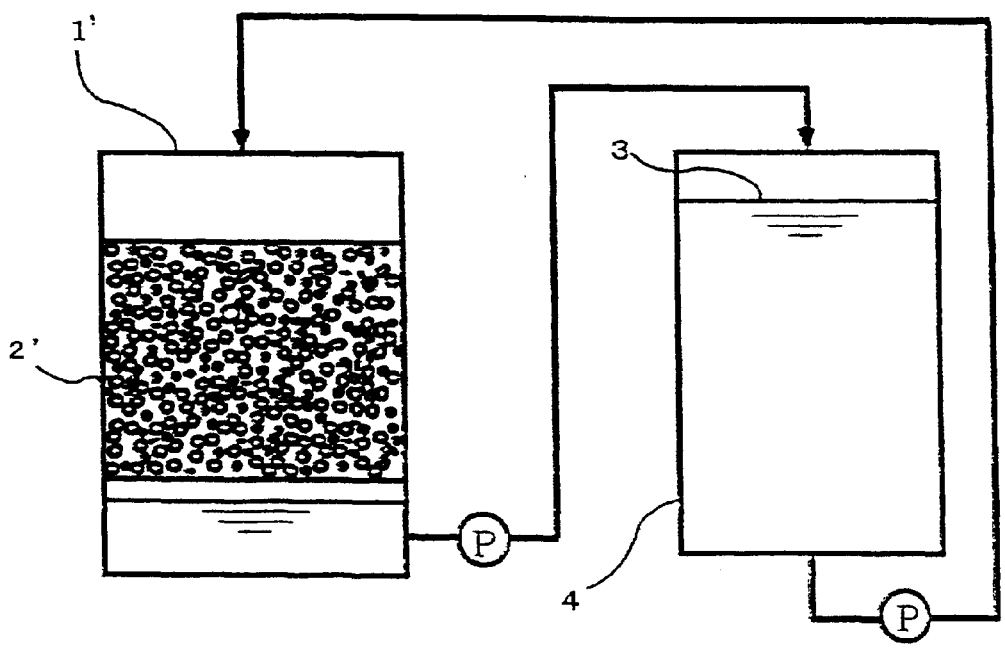
FIG. 4 is a schematic drawing of a perfusion device used in accumulation and isolation testing of the embodiments.

As shown in FIG. 4, 7.5 g of only unaccumulated artificial microhabitat B fragmented into pieces measuring 5 to 10 mm were filled into an accumulation tank having a capacity of 500 ml to form an accumulation soil layer 2'. The above accumulated artificial microhabitat B was then inoculated into this accumulation soil layer 2', the inorganic salt medium 3, having simazine for its only carbon source and nitrogen source (simazine concentration: 5 mg/l, liquid volume: 300 ml), was perfused from the liquid storage tank 4 into the accumulation soil layer 2' and accumulation was performed at 25° C. in a dark location. The perfusion liquid in the form of the inorganic salt medium 3 was replaced with fresh medium once a week, and accumulation was performed for about 3 weeks. As a result, simazine-decomposing microorganisms were accumulated in a somewhat purified state in fresh artificial microhabitat B filled with the accumulation soil layer 2'.

Next, 1.0 g of this purified accumulated artificial microhabitat B were crushed and suitably diluted with phosphate buffer solution. The thus obtained dilution was added to an inorganic salt agar medium having simazine for its only carbon source and nitrogen source. Microorganisms were then picked from the clear zones that formed on the plate media after 2 to 3 weeks of culturing, and then additionally inoculated and cultured in inorganic salt agar medium of the same composition. After repeating this procedure 2 to 3 times, 2 to 3 pieces of the portion of the clear zone that ultimately formed on the inorganic salt agar medium were cut out together with the inorganic salt agar medium and used as inoculation sources. At this time, by inoculating and culturing the clear zone portion in liquid medium having simazine as its only carbon source and nitrogen source, streaking the culture liquid onto a pre-solidified beef extract agar medium using a platinum loop, and observing the formation of single colonies, only simazine-decomposing microorganisms were confirmed to be isolated.

Adhered chlorine was then removed by washing 7.5 g each of sterilized (autoclaved), fresh artificial microhabitats A through C with sterile distilled water, fresh artificial microhabitats A through C, which had been sterilized and removed of chlorine, were respectively filled into a liquid storage tank 1' shown in FIG. 4, the accumulation soil layer 2' was formed, and the pieces previously cut out for use as inoculation sources were inoculated into the accumulation soil layer 2' as microbial strains together with the clear zones (together with inorganic salt agar medium). Subsequently, the inorganic salt medium 3, having simazine as its only carbon source and nitrogen source (simazine concentration: 5 mg/l, liquid volume: 300 ml) was perfused from the liquid storage tank 4 into the accumulation soil layer 2' and accumulation was performed at 25° C. in a dark location. The perfusion liquid in the form of the inorganic salt medium 3 was replaced with fresh medium once a week, and accumulation was performed for 3 weeks. During this accumulation treatment, simazine concentration and $Cl^-$ concentration were measured to confirm the accumulation status of simazine-decomposing microorganisms.

Although not shown specifically, in the accumulation treatments performed on each of the above fresh artificial microhabitats A through C, a phenomenon occurred in which the simazine concentration in the perfusion liquid decreased dramatically starting in week 2 of perfusion, while the concentration of $Cl^-$, a decomposition by-product of simazine, increased, clearly confirming that simazine-decomposing microorganisms were accumulated in each of the fresh artificial microhabitats A through C. However, these simazine-decomposing microorganisms were not identified.

A retentive carrier that accumulates simazine-decomposing microorganisms was formed by accumulating simazine-decomposing microorganisms in each of artificial microhabitats A through C in the manner described above. Next, an explanation is provided of the results of burying this retentive carrier for accumulating simazine-decomposing microorganisms directly in contaminated soil and testing the decomposition of simazine in the contaminated soil. The physicochemical properties of the test soil are shown in FIG. 5, and soil sampled from a golf course where simazine was used was used for the test soil. Thus, a slight amount of simazine is contained in the test soil sampled from this golf course.

Simazine was added to this test soil to a concentration of 5 mg/kg d.s. to prepare contaminated soil for decomposition. Decomposition of simazine in this contaminated soil for decomposition was performed by thoroughly mixing 0.5 g of retentive carriers accumulated with simazine-decomposing microorganisms in the form of artificial microhabitats A through C as the dry equivalent weight with 40 g of contaminated soil for decomposition followed by filling into the soil layer tank 1 shown in FIG. 3 to form a decomposition soil layer 2". After removing $Cl^-$ present in the contaminated soil for decomposition and retentive carriers accumulated with simazine-decomposing microorganisms by perfusing for 1 day with 500 ml of sterile distilled water, the inorganic salt medium 3 having simazine for its only carbon source and nitrogen source (simazine concentration: 5 mg/l, liquid volume: 300 ml) was perfused from the liquid storage tank 4 into the decomposition soil layer 2" and simazine decomposition status was confirmed at 25° C. in a dark location. Perfusion liquid in the form of the inorganic salt medium 3 was replaced with fresh medium once a week, and accumulation was performed for 3 weeks. For the sake of comparison, the decomposition soil layer 2" was also formed by thoroughly mixing artificial microhabitats not accumulated with simazine-decomposing microorganisms with contaminated soil for decomposition followed by confirmation of simazine decomposition status in the same manner as described above.

Simazine decomposition status was confirmed by measuring the concentration of simazine and the concentrations of $Cl^-$ (chloride) and $NO3^-$ (nitrate), which are the decomposition by-products of simazine, in the perfusion liquid over time. The graphs shown in FIGS. 6 through 8 indicate cases of the retentive carriers accumulated with simazine-decomposing microorganisms, while FIGS. 9 and 10 indicate cases of artificial microhabitats in which simazine-decomposing microorganisms were not accumulated.

Figure 6:
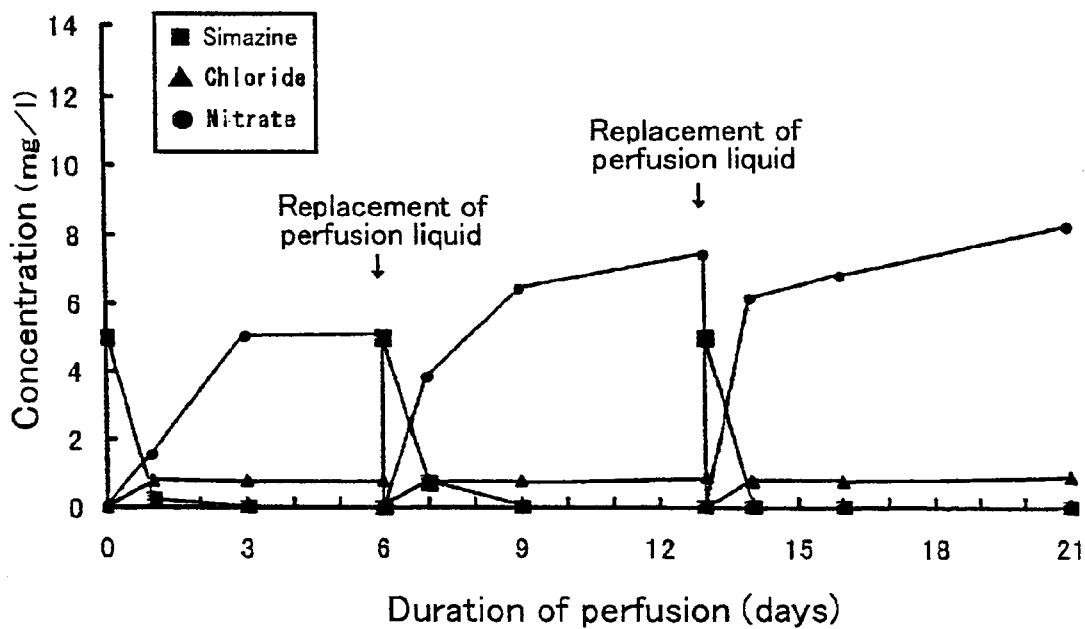
FIG. 6 is a graph showing the results of monitoring the decomposition state of simazine for simazine concentration, chloride concentration and nitrate concentration in the case of using artificial microhabitat A for the simazine decomposing microorganism retentive carrier.
Figure 7:
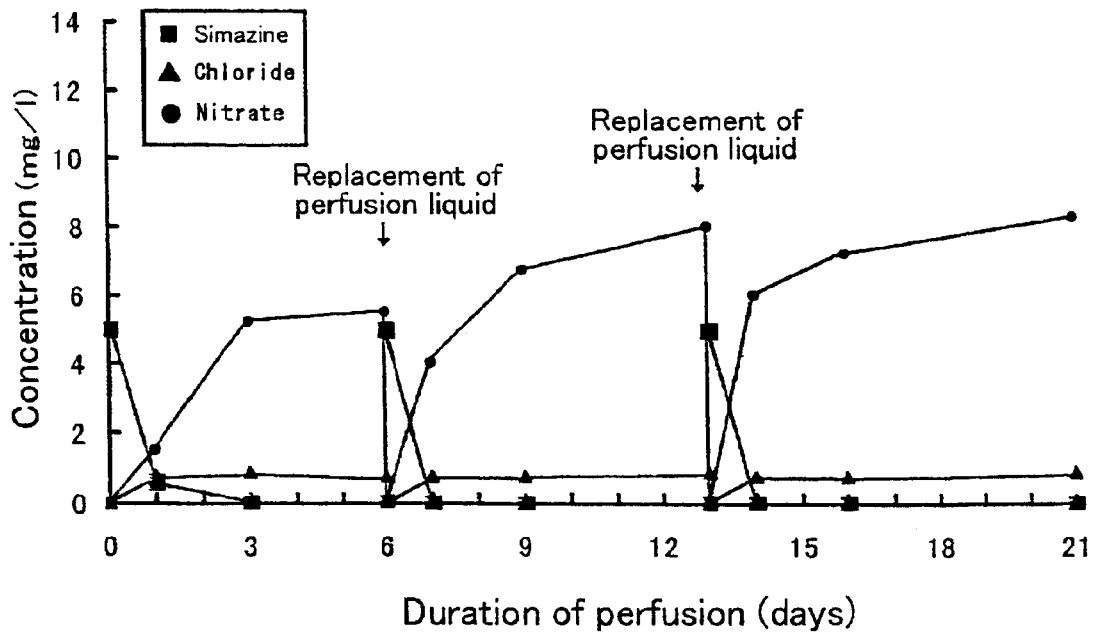
FIG. 7 is a graph showing the results of monitoring the decomposition state of simazine for simazine concentration, chloride concentration and nitrate concentration in the case of using artificial microhabitat B for the simazine decomposing microorganism retentive carrier.
Figure 8:
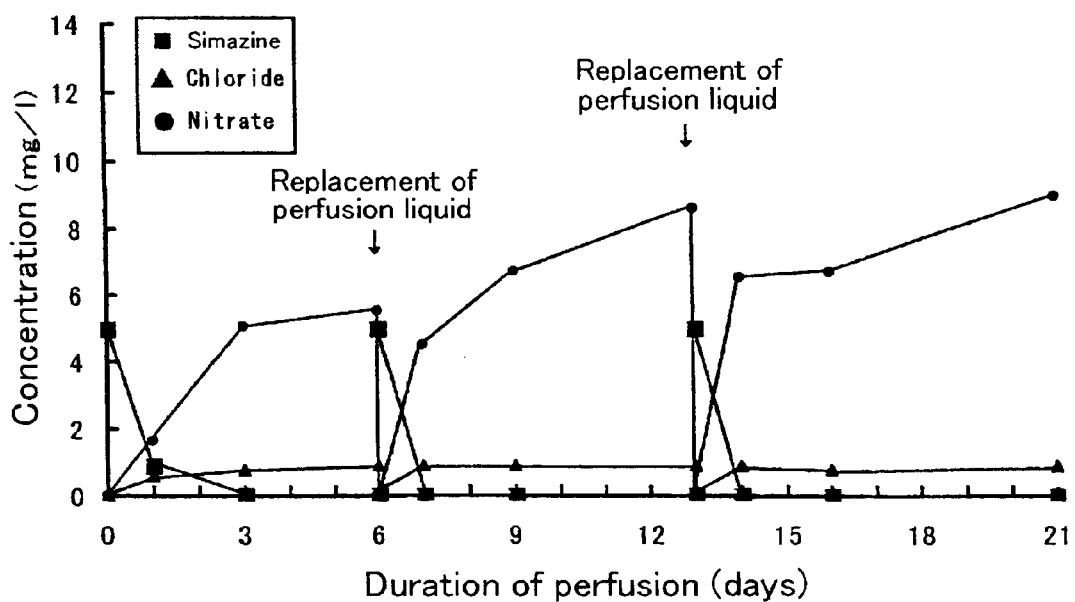
FIG. 8 is a graph showing the results of monitoring the decomposition state of simazine for simazine concentration, chloride concentration and nitrate concentration in the case of using artificial microhabitat C for the simazine decomposing microorganism retentive carrier.
Figure 9:
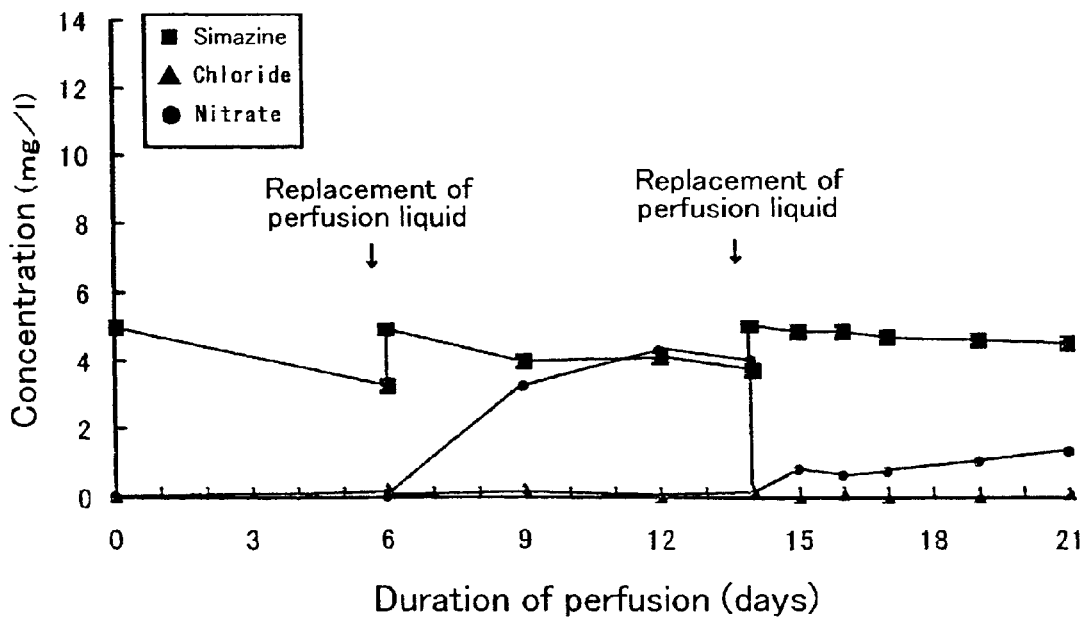
FIG. 9 is a graph showing the results of monitoring the decomposition state of simazine for simazine concentration, chloride concentration and nitrate concentration in the case of using an unaccumulated artificial microhabitat A.

FIG. 6 shows the case in which artificial microhabitat A was used for the simazine-decomposing microorganism accumulated retentive carrier, FIG. 7 shows the case in which artificial microhabitat B was used, and FIG. 8 shows the case in which artificial microhabitat C was used. FIG. 9 shows the case of using artificial microhabitat A not accumulated with simazine-decomposing microorganisms, while FIG. 10 shows the case of using artificial microhabitat B, indicated for the sake of comparison.

According to FIGS. 6 through 8, in the case of using a retentive carriers accumulated with simazine-decomposing microorganisms, simazine concentration in the perfusion liquid decreased dramatically starting with the first replacement of perfusion liquid, decreasing to a level that was hardly able to be measured. When focusing on the concentration of $Cl^-$, a by-product of simazine decomposition, the concentration value was confirmed to be nearly 0.88 mg/l, which is the theoretical concentration of Cl– produced in the case of completely decomposing 5 mg/l of simazine. On the basis of this finding, in the case of using a retentive carrier accumulated with simazine-decomposing microorganisms, it was clearly determined that simazine present in the contaminated soil for decomposition is nearly completely decomposed. In addition, as a result of measuring residual amounts of simazine in the contaminated soil for decomposition after perfusing for 3 weeks in each of the decomposition tests, the residual amounts were confirmed to be equal to or below the detection limit (0.01 mg/l).

Figure 10:
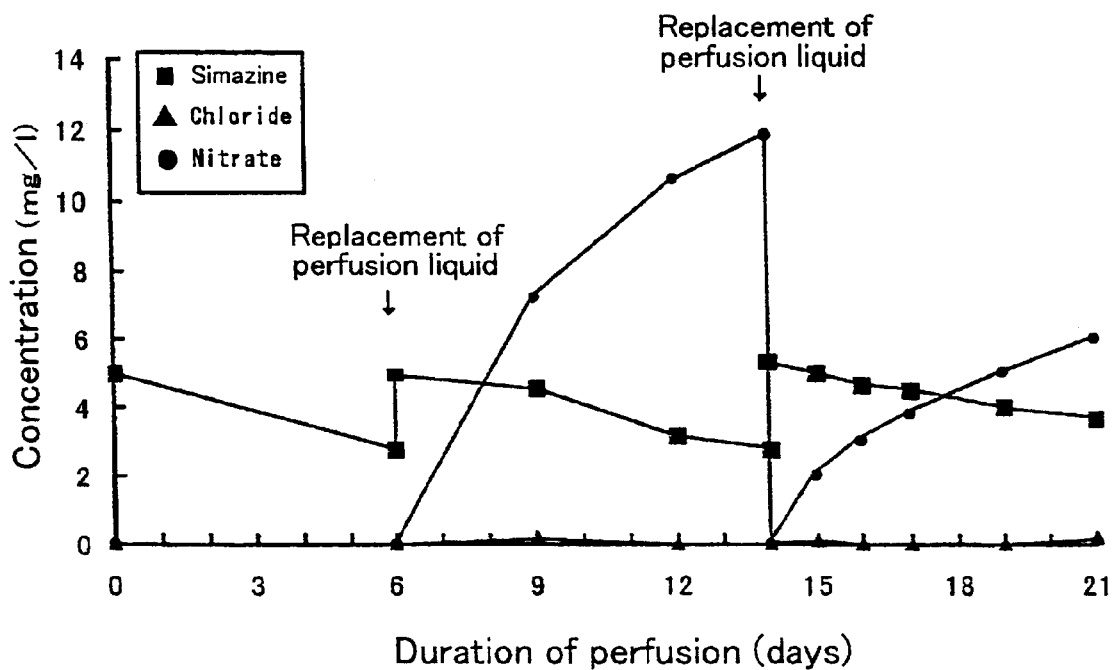
FIG. 10 is a graph showing the results of monitoring the decomposition state of simazine for simazine concentration, chloride concentration and nitrate concentration in the case of using an unaccumulated artificial microhabitat B.

On the other hand, as shown in FIGS. 9 and 10, even if unaccumulated artificial microhabitat A or B was mixed and buried in contaminated soil for decomposition, there was very little decrease in simazine concentration, and increases in the concentration of $Cl^-$, a by-product of simazine decomposition, were not confirmed. Thus, it was clearly determined that decomposition of simazine did not occur.

Figure 11:
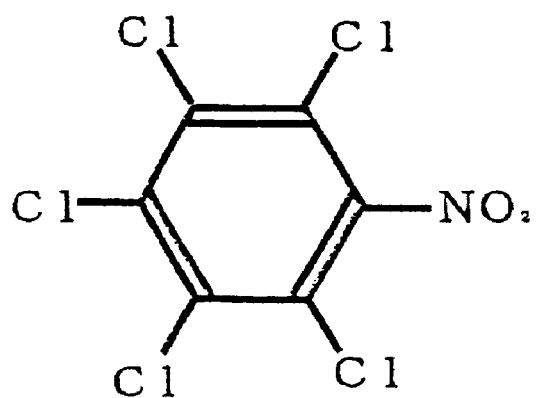
FIG. 11 is the structural formula of quintozene.

Next, an explanation is provided of the case of the poorly degradable organic chlorine-based agricultural chemical, quintozene (PCNB), as a second example of the present invention. The structural formula of quintozene is shown in FIG. 11.

SECOND EXAMPLE

The procedures for accumulation and isolation of quintozene along with the formation of retentive carriers accumulated with quintozene-decomposing microorganisms were performed using the same procedures as those explained for simazine in the first example. In other words, since quintozene can be used in place of simazine in the explanation of the first example, a detailed explanation is omitted here. However, contaminated soil for decomposition of quintozene was sampled from the same golf course as in the case of simazine and used as the test soil, and prepared by adding quintozene to a concentration of 10 mg/kg d.s. In addition, the perfusion liquid used had a quintozene concentration of 0.5 mg/l.

Figure 12:
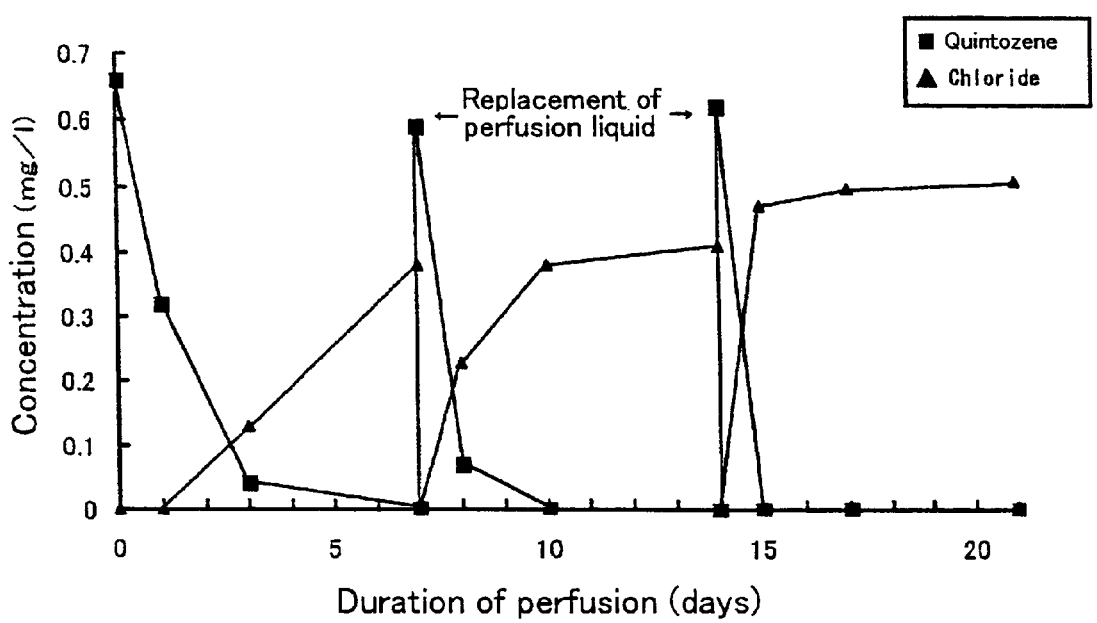
FIG. 12 is a graph showing the results of monitoring the decomposition state of quintozene for quintozene concentration, chloride concentration and nitrate concentration in the case of using artificial microhabitat A for the quintozene decomposing microorganism retentive carrier.
Figure 13:
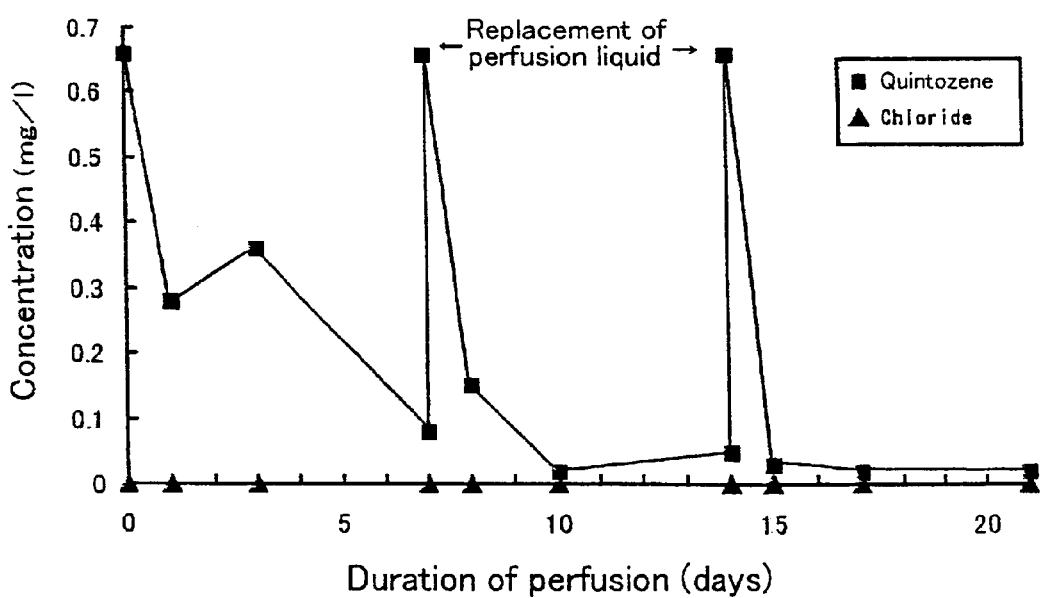
FIG. 13 is a graph showing the results of monitoring the decomposition state of quintozene for quintozene concentration, chloride concentration and nitrate concentration in the case of using an unaccumulated artificial microhabitat A.

FIGS. 12 and 13 show the results of decomposition testing in which the decomposition status of quintozene was observed. FIG. 12 indicates the case of using artificial microhabitat A for the retentive carrier accumulated with quintozene-decomposing microorganisms, while FIG. 13 indicates the case of using artificial microhabitat A not accumulated with quintozene-decomposing microorganisms as a comparative example.

As shown in FIG. 12, in the case of using a quintozene-decomposing microorganism accumulated retentive carrier, quintozene concentration in the perfusion liquid decreased dramatically following the first replacement of perfusion liquid, and following the second replacement of perfusion liquid, hardly any quintozene was detected. In addition, when focusing on the concentration of $Cl^-$, a by-product of quintozene decomposition, since the concentration value was confirmed to exceed 0.3 mg/l, which is the theoretical concentration of $Cl^-$ produced in the case of complete decomposition of 0.5 mg/l of quintozene, quintozene was clearly demonstrated to be completely decomposed. On the other hand, as shown in FIG. 13, even when artificial microhabitat A not accumulated with quintozene-decomposing microorganisms was mixed with the test soil for decomposition, although quintozene concentration demonstrated a decreasing trend, since there was no increase whatsoever confirmed for the concentration of $Cl^-$, a by-product of quintozene decomposition, it was clearly determined that hardly any quintozene was decomposed.

FIG. 14 shows the results of evaluating the residual amounts of quintozene contained in each contaminated soil for decomposition, retentive carrier accumulated with quintozene-decomposing microorganisms, and for the sake of comparison, artificial microhabitat A not accumulated with quintozene-decomposing microorganisms, following the perfusion treatment for the decomposition testing of quintozene shown in FIGS. 12 and 13. As shown in FIG. 14, the contaminated soil for decomposition in which quintozene was decomposed contained an initial concentration of quintozene of 10 mg/kg d.s. However, only an extremely small amount of 0.035 mg/kg d.s. of quintozene remained in the contaminated soil for decomposition after decomposition testing was performed using the retentive carrier accumulated with quintozene-decomposing microorganisms. In addition, the retentive carrier accumulated with quintozene-decomposing microorganisms that was buried in the contaminated soil for decomposition was confirmed to hardly contain any quintozene, with only 0.004 mg/kg d.s. remaining. Accordingly, in the case of using a retentive carrier accumulated with quintozene-decomposing microorganisms, the decomposition removal rate of quintozene was clearly determined to be 99.61%. On the other hand, in the case of using unaccumulated artificial microhabitat A as a comparative example, 8.70 mg/kg d.s. of quintozene remained in the contaminated soil for decomposition after decomposition testing, and 0.32 mg/kg d.s. of quintozene was confirmed to remain in unaccumulated artificial microhabitat A. Calculation of the decomposition removal rate in this case only resulted in a value of 9.84%, thereby confirming that hardly any of the quintozene was decomposed.

Moreover, an explanation is provided of the results of evaluating the presence of decomposing microorganisms in the perfusion liquid. FIG. 15 shows the results of measuring the weekly counts of quintozene-decomposing microorganisms contained in each perfusion liquid in the decomposition testing of quintozene shown in FIGS. 12 and 13. As can be understood by looking at FIG. 15, quintozene-decomposing microorganisms were not confirmed in the perfusion liquid in either case. Consequently, it was clearly determined that microorganisms that decompose quintozene are not dispersed in the soil as a result of leaving the artificial microhabitat. Thus, even if the retentive carrier accumulated with decomposing microorganisms in the present example is buried directly in contaminated soil, since quintozene-decomposing microorganisms themselves do not leave the retentive carrier, it was confirmed that there is no occurrence of contamination of ground water by bacteria.

Finally, an explanation is provided of the decomposing microorganisms that decompose quintozene. As a result of completing identification of these decomposing microorganisms, the inventors of the present invention determined that these decomposing microorganisms were *Burkholderia cepacia* KTYY97 (deposition date: May 18, 1998, National Institute of Bio-science and Human Technology, domestic deposition no. FERM P-16809, later followed by transfer of control to international deposition on May 14, 1999 and changed to international deposition no. FERM BP-6721). The characteristics of this microorganism are described by the authors of the present invention in Japanese Patent Application No. Hei 10-135156 (Japanese Patent No. 2904432).

INDUSTRIAL APPLICABILITY

As has been described above, according to the present invention, a decomposing microorganism of a species that is able to decompose a specific organic compound can be rapidly and efficiently isolated and accumulated in a state in which decomposition activity is demonstrated in a stable manner and for a long period of time. By applying a decomposing microorganism retentive carrier in which that decomposing microorganism has been accumulated directly to contaminated soil, the organic compound in the contaminated soil is decomposed, and the contaminated soil can be restored or contamination of ground water can be prevented both rapidly and efficiently, thereby enabling the present invention to promote restoration of a contaminated environment (bioremediation).

What is claimed is:

1. A method for accumulating isolated decomposing microorganisms, comprising:

accumulating microorganisms of a species able to decompose a specific organic compound in a porous material that is able to adsorb said organic compound while also having pores that facilitate habitation by said microorganisms; wherein, said decomposing microorganisms are accumulated in said porous material by inoculating only said microorganisms into said porous material, forming an accumulation layer composed of said inoculated porous material, and perfusing an inorganic salt medium having only said organic compound for its carbon source and nitrogen source into said accumulation layer.

2. The method according to claim 1, wherein the only microorganisms that are inoculated have been isolated by inoculating a group of bacteria that includes microorganisms of a species able to decompose said specific organic compound into an inorganic salt agar medium having only said organic compound for its carbon source and nitrogen source, and picking said microorganisms from a clear zone formed in said inorganic salt agar medium.

3. The method according to claim 2, wherein the specific organic compound is an organic contaminant able to be contained in soil, and the group of bacteria that includes microorganisms of a species able to decompose said organic contaminant is accumulated by mixing a porous material into soil in which the microorganisms of a species able to decompose said organic contaminant thrive to form an accumulation soil layer, accumulating said microorganisms in said porous material by perfusing an inorganic salt medium having only said organic contaminant for its carbon source and nitrogen source into this accumulation soil layer, removing this accumulated porous material from the accumulation soil layer, performing washing treatment on this removed accumulated porous material to remove adhered soil, using this washed accumulated porous material as an inoculation source to inoculate an accumulation layer formed only with a fresh porous material and purifying said microorganisms in this fresh porous material by perfusing an inorganic salt medium having only said organic contaminant for its carbons source and nitrogen source into that accumulation layer.

4. The method according to claim 3, wherein the organic contaminant is an organic chlorine-based compound.

5. A microorganism retentive carrier that has retained microorganisms of a species able to decompose a specific organic compound obtained according to the accumulation method for isolated microorganisms as set forth in any one of claims 1 through 4.

6. A method for contaminated soil restoration or ground water contamination prevention that restores contaminated soil or prevents contamination of ground water by an organic compound in the soil by decomposing said organic compound in contaminated soil using the microorganism retentive carrier according to claim 5; wherein, contaminated soil is restored or contamination of ground water is prevented by burying said microorganism retentive carrier in contaminated soil containing a specific organic compound to decompose the organic compound present in said contaminated soil.

* * * * *